United States Patent [19]

Gramlich et al.

[11] Patent Number: 4,464,370

[45] Date of Patent: Aug. 7, 1984

[54] CYCLOHEXENE CONTAINING MORPHOLINES AND FUNGICIDAL USE

[75] Inventors: Walter Gramlich, Edingen; Walter Himmele, Walldorf; Christoph Martin, Mannheim; Ernst-Heinrich Pommer, Limburgerhof; Hardo Siegel, Speyer, all of Fed. Rep. of Germany

[73] Assignee: BASF Aktiengesellschaft, Fed. Rep. of Germany

[21] Appl. No.: 380,470

[22] Filed: May 20, 1982

[30] Foreign Application Priority Data

May 29, 1981 [DE] Fed. Rep. of Germany ....... 3121349

[51] Int. Cl.³ ............... A01N 43/84; C07D 295/02
[52] U.S. Cl. ................. 424/248.4; 544/178; 546/192
[58] Field of Search .............. 544/170, 171, 178; 546/192, 238, 240; 260/239 B; 424/244, 248.4, 248.57, 267, 248.55

[56] References Cited

U.S. PATENT DOCUMENTS 3,423,406  1/1969  Mull et al. ............... 260/240
4,241,058  12/1980  Pfiffner ................... 544/178

FOREIGN PATENT DOCUMENTS 8686     3/1980  European Pat. Off. .
1584290  2/1981  United Kingdom .
1591267  6/1981  United Kingdom .

Primary Examiner—Robert W. Ramsuer
Attorney, Agent, or Firm—Keil & Weinkauf

[57] ABSTRACT

Cyclohexene derivatives of the formula I

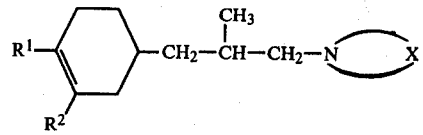

where $R^1$ and $R^2$ are hydrogen or tert.-butyl and N and X are members of a heterocyclic ring in which X is an alkylene chain of four, five or six members, one of which may be a hetero-atom, such as oxygen, and where the alkylene radicals are unsubstituted or substituted by alkyl or by —$CH_2OH$ or its acetyl or propionyl derivative, and their salts are used in fungicides.

4 Claims, No Drawings

CYCLOHEXENE CONTAINING MORPHOLINES AND FUNGICIDAL USE

The present invention relates to novel useful 3-cyclohexen-3'-yl-2-methyl-prop-1-yl-cycloalkylamine derivatives, processes for their preparation, fungicides containing these derivatives and methods of controlling fungi.

German Laid-Open Applications DOS No. 2,656,747 and DOS No. 2,752,135 disclose that 4-[3-(p-tert.-butyl-phenyl)-2-methylpropyl]-cis-2,6-dimethyl-morpholine can be used for controlling powdery mildew and rust fungi in cereals, especially in wheat. It is also possible to use compounds which, instead of the 2,6-dimethylmorpholine radical, contain radicals of other cyclic amines, such as piperidine or 3-methylpiperidine, or which, instead of the tert.-butylphenyl radical, contain the tert.-butylcyclohexyl radical. These compounds provide complete protection against the harmful fungi for a period of from three to four weeks. It is frequently necessary to re-apply the fungicide.

German Laid-Open Application DOS No. 3,001,581 discloses fungicidal N-[3-(4'-tert.-butylcyclohex-1'-en-1'-yl)-2-methylprop-1-yl]-cycloalkylamines which are obtained by partial hydrogenation of the corresponding aromatic compounds disclosed in German Laid-Open Applications DOS No. 2,656,747 and DOS No. 2,752,135. However, this preparation procedure gives a yield of only about 20%, and the separation of the partially hydrogenated products from the aromatic starting compounds and from the perhydrogenated cis- and trans-forms obtained at the same time entails very great expense (distillation). In the resulting cyclohexene compounds of the formula IV

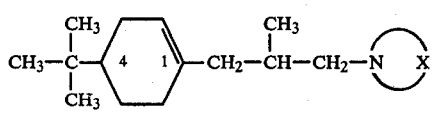

the double bond is on carbon atom 1.

We have found that cyclohexene derivatives of the formula I

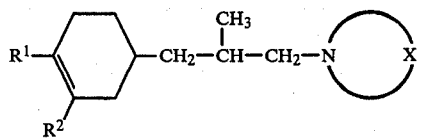

where $R^1$ and $R^2$ differ and each is hydrogen or tert.-butyl and N and X are members of a five-membered, six-membered or seven-membered heterocyclic ring in which X is an alkylene chain of four, five or six members, one of which may be a hetero-atom, such as oxygen, and where the alkylene radicals are unsubstituted or mono- or polysubstituted by alkyl of 1 to 4 carbon atoms or by —CH$_2$OH or its acetyl or propionyl derivative, and their salts have a good fungicidal action.

An example of an alkylene radical is methylene. Examples of alkyl of 1 to 4 carbon atoms are methyl, ethyl, propyl, iso-butyl, sec.-butyl and n-butyl. Examples of salts are non-phytotoxic salts with inorganic or organic acids, eg. hydrogen halide acids, such as hydrochloric acid or hydrobromic acid, mineral acids, such as sulfuric acid or phosphoric acid, and carboxylic acids, such as acetic acid or propionic acid.

The proviso that $R^1$ and $R^2$ differ means that, in a particular compound, $R^1$ and $R^2$ are not simultaneously hydrogen and not simultaneously each tert.-butyl.

Very good yields of the novel compounds are obtained in a simple manner by reacting a compound of the formula II

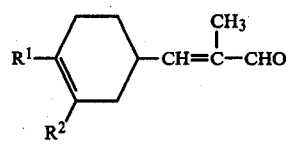

where $R^1$ and $R^2$ have the above meanings, with hydrogen in the presence of an amine of the formula III

where N and X have the above meanings, and in the presence of a hydrogenation catalyst, and, if appropriate, converting the resulting compound into its salt.

The compounds of the formula II are accessible, for example, as follows:

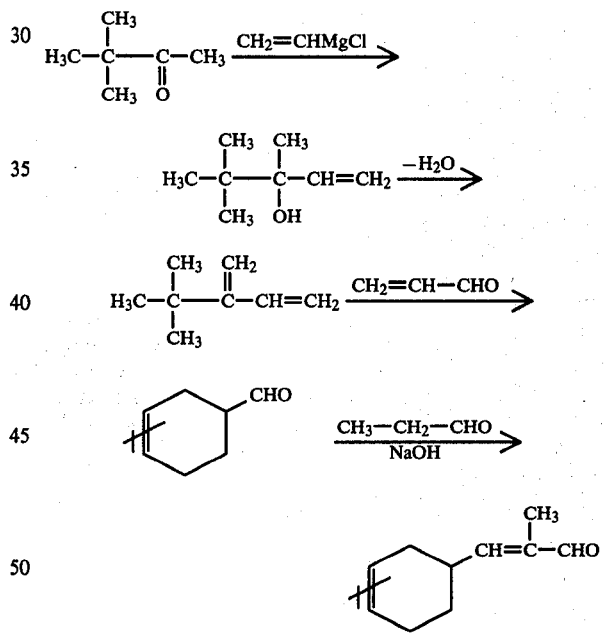

$\nearrow$ = tert.-butyl

Surprisingly, during further reaction with hydrogen and with amines of the formula III in the presence of a hydrogenation catalyst to give the compounds of the formula I, the double bond at the position shown in the cyclohexene ring is retained entirely, while the double bond in the side chain is hydrogenated. Examples of suitable amines are pyrrolidine, morpholine, thiomorpholine, 2,6-dimethylmorpholine (cis/trans mixture), cis-2,6-dimethylmorpholine, 2,5-dimethylmorpholine, piperidine, 3,5-dimethylpiperidine, 3-methylpiperidine, 3,4-dimethylpiperidine, 3-ethyl-4-methylpiperidine, 3-methyl-4-ethylpiperidine, 2,6-dimethylpiperidine, hexamethyleneimine, 2-methylhexamethyleneimine and 3-methylhexamethyleneimine. Palladium and rhodium are particularly suitable catalysts for the reaction, but palladium on an inert carrier, such as $Al_2O_3$, $TiO_2$, charcoal and the like, is preferred. Natural or synthetic silicates, such as aluminum silicates or magnesium silicate, are also suitable carriers.

The reaction is carried out at from 25° to 180° C., preferably from 30° to 110° C., under a hydrogen pressure of from 2 to 100 bar.

The compounds of the formula I contain an asymmetric carbon atom. The invention relates both to the racemates and to the individual optically active forms.

The optically active forms are obtained by resolving the fungicidal amines of the formula I with optically active acids in a conventional manner. In another advantageous process, a compound of the formula II is reduced with yeast in a fermenter to give the optically active alcohol V, from which the compound VI can be prepared in a conventional manner.

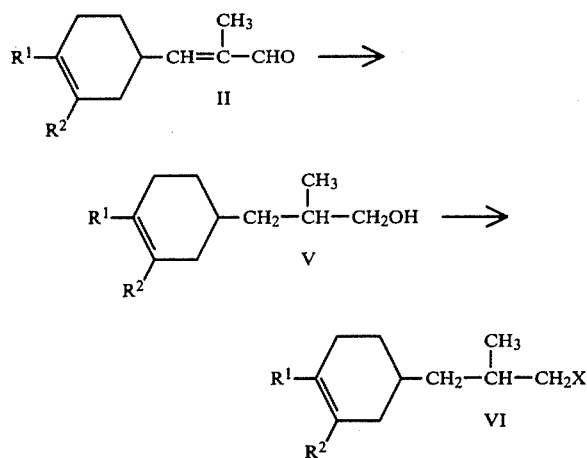

In the formulae II, V and VI, $R^1$ and $R^2$ have the above meanings and X is halogen, such as chlorine or bromine, or istosyl or mesyl. A compound of the formula VI can be reacted with an amine of the formula III in a conventional manner to give a fungicidal compound of the formula I.

The instructions and Examples which follow illustrate the preparation of the intermediate and end products.

METHOD A tert.-Butylbutadiene 30 g of oxalic acid, 50 ml of water and 2 g of hydroquinone are added to 1 mole of methyl-vinyl-tert.-butylcarbinol, which has been prepared in a conventional manner from a vinyl-magnesium chloride solution in tetrahydrofuran and methyl tert.-butyl ketone. The mixture is refluxed for 30 minutes and the tert.-butylbutadiene formed is then slowly distilled off, together with water. The yield is 92 g.

METHOD B tert.-Butyl-cyclohexenecarboxaldehyde ($\Delta^3$-tert.-butyl-tetrahydrobenzaldehyde)

Molar amounts of tert.-butylbutadiene and acrolein are refluxed for 6–8 hours. A mixture of about 70% of 4-tert.-butyl-cyclohex-3-ene-1-carboxaldehyde and about 30% of 3-tert.-butyl-cyclohex-3-ene-1-carboxaldehyde is obtained in a yield of about 80%. Boiling point: 112° C./28 mbar.

METHOD C

A mixture of $\Delta^3$-4-tert.-butyl- and $\Delta^3$-3-tert.-butyl-tetrahydrobenzaldehyde prepared according to instructions B is condensed with propionaldehyde in a conventional manner. An 80% yield of 2-methyl-(4-tert.-butyl-cyclohex-3-enyl)-prop-2-en-1-al and 2-methyl-(3-tert.-butyl-cyclohex-3-enyl)-prop-2-en-1-al in a ratio of about 70:30 is obtained. Boiling point: 153° C./30 mbar.

EXAMPLE 1

73 g of a mixture prepared according to instructions C were dissolved in 500 g of methanol, 40 g of cis-2,6-dimethylmorpholine were added and the mixture was reacted with $H_2$ at 50 bar in a stirred autoclave at 40° C. in the presence of 7.8 g of $\gamma$-$Al_2O_3$ containing 0.5% of Pd, until the uptake of hydrogen fell to below 1 bar/hour. The mixture was then post-hydrogenated for a further 3 hours at 100° C. and under 50 bar of $H_2$. The discharge was worked up by distillation to give an a yield of about 75% of a mixture of N-(3-[4'-tert.-butyl-cyclohex-3'-enyl]-2-methyl-prop-1-yl)-cis-2,6-dimethylmorpholine and the corresponding 3'-tert.-butyl compound in a ratio of 70:30. Boiling point: 142°–144° C./1 mbar.

EXAMPLE 2

The amine mixture from Example 1 was converted into the hydrochloride in an inert solvent by gassing with dry HCl gas, and the hydrochloride was recrystallized from methanol (melting point: 190° C.) and converted into the base again with alkali. Pure N-(3-[4'-tert.-butyl-cyclohex-3'-enyl]-2-methyl-prop-1-yl)-cis-2,6-dimethylmorpholine was obtained. Boiling point: 125° C./0.25 mbar. The 3'-tert.-butyl isomer could no longer be detected by spectroscopy.

EXAMPLE 3

A mixture prepared according to instructions C was hydrogenated with yeast. A clean, unsterilized fermenter having a total volume of 6 l was charged as follows:

| | |
|---|---|
| completely demineralized water | 1.8 l |
| sucrose | 90 g |
| pressed yeast (Deutsche Hefewerke) | 200 g |
| mixture according to Method C | 8 g in 30 ml of ethanol |
| silicone anti-foam | 2 g |

The fermentation conditions were as follows:

| | |
|---|---|
| temperature: | 30° C. |
| stirrer speed: | 500 rpm |
| rate of aeration: | 1 VVM |
| fermentation time: | 52.5 hours |

The fermentation was discontinued after 52.5 hours. The cell mass was separated off from the nutrient solution by centrifugation, and both phases were extracted 3 times with methylene chloride. The combined extracts were dried over $Na_2SO_4$ and evaporated under reduced pressure, and the residue was distilled to give a levorotatory mixture of 2-methyl-[4-tert.-butyl-cyclohex-3- enyl]-propan-1-ol and 2-methyl-[3-tert.-butyl-cyclohex-3-enyl]-propan-1-ol in a ratio of 70:30. This mixture was converted into the tosylate, and the tosylate was reacted with cis-2,6-dimethylmorpholine. The same mixture as in Example 1 was obtained, but in the optically active form with an $\alpha_D{}^{20}$ of $-2.6°$ (pure).

EXAMPLE 4

The procedure followed was as described in Example 1, and the following fungicidal amines (mixtures) were obtained:

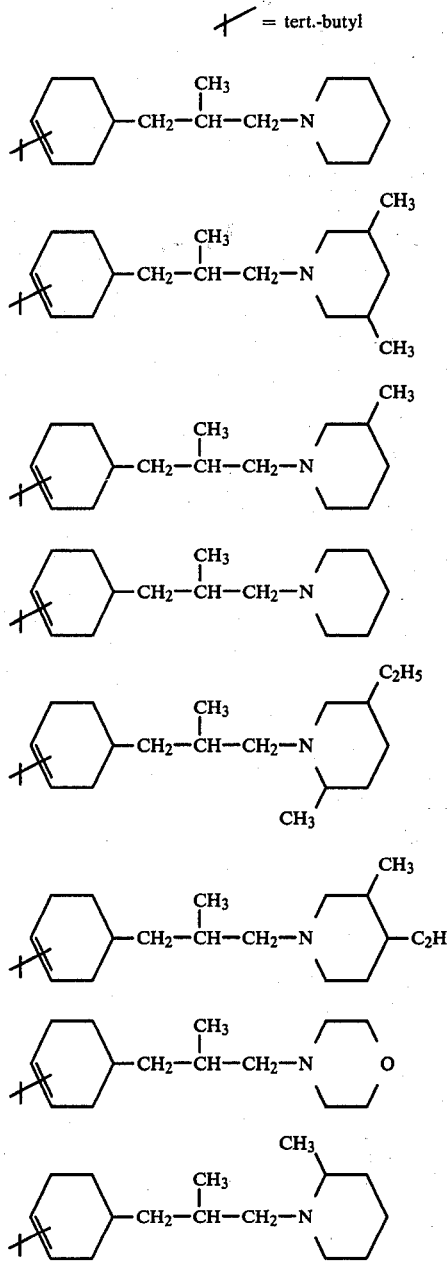

The 4-tert-butyl compounds according to Example 2 may be isolated from this mixture in pure form.

The novel compounds are especially suitable for combating plant diseases, e.g., *Erysiphe graminis* in cereals, *Erysiphe cichoriacearum* in Cucurbitaceae, *Podosphaera leucotricha* in applies, *Uncinula necator* in grapes, *Erysiphe polygoni* in beans, *Sphaerotheca pannosa* in roses, *Microsphaera querci* in oaks, *Botrytis cinerea* in strawberries and grapes, *Mycosphaerella musicola* in bananas, *Puccinia* species (rusts) in cereals, *Uromyces appendiculatus* and *U. phaseoli* in beans, *Hemileia vastatrix* in coffee and *Rhizoctonia solani*. They have a systemic action—they are taken up through the roots and via the leaves and are translocated in the plant tissue.

For the following experiment, the prior art active ingredient 4-[3-(p-tert-butylcyclohexyl)-2-methylpropyl]-cis-2,6-dimethylmorpholine A (German Laid-Open Application DE-OS No. 2,921,131) was used for comparison purposes.

ACTION ON RHIZOCTONIA SOLANI

Cotton seeds of the "Delta Pine" variety were thoroughly dusted with 0.3 g per 100 g of seed of a seed dressing formulation containing, in triturated form, 40% (wt%) of the candidate compound and 60% of talc. The seeds treated in this manner were then placed in pots and covered with soil which had previously been artificially inoculated with the fungus *Rhizoctonia solani*. The spread of the disease compared with a prior art fungicide and an untreated control was assessed after 21 days. The results revealed that the compositions of Examples 1 and 3 had, 21 days after emergence of the cotton plants, a good fungicidal action, and prior art compound A only had a slight fungicidal action.

ACTION ON WHEAT MILDEW

Leaves of pot-grown wheat seedlings of the "Jubilar" variety were sprayed with aqueous emulsions consisting of 80% (wt%) of active ingredient and 20% of emulsifier (sodium lignin sulfonate), and dusted, after the sprayed-on layer had dried, with oidia of wheat mildew (Erysiphe graminis var. tritici). The plants were then set up in the greenhouse at from 20° to 22° C. and a relative humidity of 75 to 80%. The extent of fungus spread was determined after 10 days.

The results revealed that the active ingredients prepared according to Example 1 (composition), 2 and 3 (composition) had a good fungicidal action.

When the active ingredients are used to treat plants against fungus infection, application rates are from 0.025 to 5 kg of active ingredient per hectare. For the surface protection of trees or fruit, the active ingredients may also be employed together with plastics dispersions, in amounts of from 0.25 to 5%, based on the weight of the dispersion. The fungicides generally contain from 0.1 to 95, and preferably from 0.5 to 90, wt% of active ingredient.

The active ingredients are also suitable for combating wood-destroying fungi, such as *Coniophora puteana*, *Poria vaporaria*, *Lenzites trabea* and *Polystictus versicolor*. Solvent-containing wood preservative formulations may contain, for instance, from 0.5 to 2 wt% of active ingredient.

The agents according to the invention may also be mixed and applied with other, prior art, fungicides. In many instances, the spectrum of fungicidal action is increased; with a number of these fungicidal compositions at weight ratios of 1:10 to 10:1, synergistic effects also occur; i.e., the fungicidal action of the combination product is greater than the effect of the individual components added together.

Examples of fungicides which may be combined with the compounds according to the invention are: dithiocarbamates and their derivatives, e.g. zinc dimethyldithiocarbamate, manganese N,N-ethylene-bis-dithiocarbamate, manganese zinc N,N-ethylenediamine-bis-dithiocarbamate, zinc N,N-ethylene-bis-dithiocarbamate, tetramethylthiuram disulfide, the ammonia complex of zinc N,N-ethylene-bis-dithiocarbamate and N,N'-polyethylene-bis-(thiocarbamoyl)-disulfide, zinc N,N'-propylene-bis-dithiocarbamate, and the ammonia complex of zinc N,N'-propylene-bis-dithiocarbamate and N,N'-polypropylene-bis-(thiocarbamoyl)-disulfide; heterocyclic compounds, e.g. N-trichloromethylthiotetrahydrophthalimide, N-trichloromethylthio-phthalimide, N-(1,1,2,2-tetrachloroethylthio)-tetrahydrophthalimide, methyl 1-(butylcarbamoyl)-2-benzimidazolecarbamate, 2-methoxycarbonylamino-benzimidazole, 2,3-dihydro-5-carboxanilido-6-methyl-1,4-oxathiine-4,4-dioxide, 2,3-dihydro-5-carboxanilido-6-methyl-1,4-oxathiine, 5-butyl-2-dimethylamino-4-hydroxy-6-methyl-pyrimidine, 1,2-bis-(3-ethoxycarbonyl-2-thioureido)-benzene, 1,2-bis-(3-methoxycarbonyl-2-thioureido)-benzene and various other fungicides, e.g. dodecylguanidine acetate, N-dichlorofluoromethylthio-N',N'-dimethyl-N-phenyl-sulfuric acid diamide, 2,5-dimethylfuran-3-carboxylic acid anilide, 2,5-dimethylfuran-3-carboxylic acid cyclohexylamide, 2-bromo-benzoic acid anilide, 2-iodo-benzoic acid anilide, diisopropyl 3-nitroisophthalate, 1-(1,2,4-triazol-1'-yl)-[1-(4'-chlorophenoxy)]-3,3-dimethylbutan-2-one, 1-(1-imidazolyl)-2-allyloxy-2-(2,4-dichlorophenyl)-ethane, piperazine-1,4-diyl-bis-1-(2,2,2-trichloroethyl)-formamide, 2,4,5,6-tetrachloroisophthalonitrile, and 1,2-dimethyl-3,5-diphenyl-pyrazolinium methyl sulfate.

Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable. The salts may be used as aqueous solutions.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

Oils of various types, herbicides, fungicides, nematicides, insecticides, bactericides, trace elements, fertilizers, antifoams (e.g., silicones), growth regulators, antidotes or other active compounds may be added to the individual active ingredients or mixtures thereof.

EXAMPLE I 20 parts of the compound of Example 1 is intimately mixed with 12 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

EXAMPLE II 3 parts by weight of the compound of Example 2 is intimately mixed with 97 parts by weight of particulate kaolin. A dust is obtained containing 3% by weight of the active ingredient.

EXAMPLE III 30 parts by weight of the compound of Example 3 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE IV 40 parts by weight of the compound of Example 1 is intimately mixed with 10 parts of the sodium salt of a phenolsulfonic acid-urea-formaldehyde condensate, 2 parts of silica gel and 48 parts of water to give a stable aqueous dispersion.

EXAMPLE V 20 parts by weight of the compound of Example 2 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil.

EXAMPLE VI 20 parts by weight of the compound of Example 3 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil.

EXAMPLE VII 20 parts by weight of the compound of Example 1 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill.

We claim:

1. A cyclohexene derivative of the formula

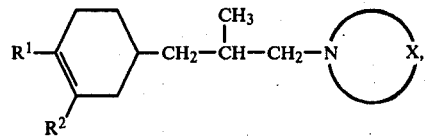

where $R^1$ and $R^2$ are different and each is hydrogen or tert.-butyl and N and X are members of a morpholine ring and where the morpholine ring is unsubstituted or mono- or polysubstituted by alkyl of 1 to 4 carbon atoms or a salt thereof.

2. A process for combating fungi, wherein the fungi or the objects to be protected against fungus attack are treated with a cyclohexene derivative of the formula

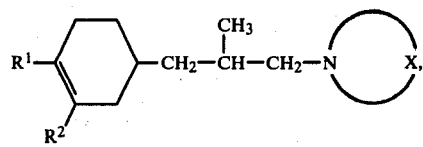

where $R^1$ and $R^2$ are different and each is hydrogen or tert.-butyl and N and X are members of a morpholine ring and where the morpholine ring is unsubstituted or mono- or polysubstituted by alkyl of 1 to 4 carbon atoms or a salt thereof.

3. N-(3-[4'-tert-butyl-cyclohex-3'-enyl]-2-methyl-prop-1-yl)-2,6-dimethylmorpholine.

4. N-(3-[4'-tert-butyl-cyclohex-3'-enyl]-2-methyl-prop-1-yl)-cis-2,6-dimethylmorpholine.

* * * * *